(12) United States Patent
Murakami et al.

(10) Patent No.: US 11,066,367 B2
(45) Date of Patent: Jul. 20, 2021

(54) ELECTRON DONOR, AND METHOD FOR SYNTHESIZING 4, 4'-BIPYRIDINE USING ELECTRON DONOR

(71) Applicants: KOBELCO ECO-SOLUTIONS CO., LTD., Hyogo (JP); NATIONAL UNIVERSITY CORPORATION OKAYAMA UNIVERSITY, Okayama (JP)

(72) Inventors: Yoshiaki Murakami, Hyogo (JP); Miyuki Fukushima, Hyogo (JP); Kazuhiko Takai, Okayama (JP); Sobi Asako, Okayama (JP)

(73) Assignee: Kobelco Eco-Solutions Co., Ltd., Hyogo (JP)

(*) Notice: Subject to any disclaimer, the term of this patent is extended or adjusted under 35 U.S.C. 154(b) by 0 days.

(21) Appl. No.: 16/651,134

(22) PCT Filed: Sep. 27, 2018

(86) PCT No.: PCT/JP2018/035873
§ 371 (c)(1),
(2) Date: Mar. 26, 2020

(87) PCT Pub. No.: WO2019/065811
PCT Pub. Date: Apr. 4, 2019

(65) Prior Publication Data
US 2020/0270212 A1 Aug. 27, 2020

(30) Foreign Application Priority Data
Sep. 28, 2017 (JP) .............................. JP2017-188320

(51) Int. Cl.
| | | |
|---|---|---|
| *C07D 213/22* | (2006.01) | |
| *B01J 23/04* | (2006.01) | |
| *B01J 31/02* | (2006.01) | |
| *B01J 35/12* | (2006.01) | |
| *C07D 233/54* | (2006.01) | |

(52) U.S. Cl.
CPC ............ *C07D 213/22* (2013.01); *B01J 23/04* (2013.01); *B01J 31/0244* (2013.01); *B01J 35/12* (2013.01)

(58) Field of Classification Search
None
See application file for complete search history.

(56) References Cited

U.S. PATENT DOCUMENTS

| | | | |
|---|---|---|---|
| 4,194,046 A | 3/1980 | Junghans | |
| 5,593,463 A | 1/1997 | Gambini et al. | |
| 5,593,464 A * | 1/1997 | Cook ..................... | C10L 1/188 44/362 |
| 10,544,098 B2 * | 1/2020 | Murakami ......... | C07D 213/127 |
| 2018/0282278 A1 | 10/2018 | Murakami et al. | |

FOREIGN PATENT DOCUMENTS

| | | |
|---|---|---|
| CN | 1158852 A | 9/1997 |
| GB | 957098 A | 5/1964 |
| JP | 55-24154 A | 2/1980 |
| JP | H01-211532 A | 8/1989 |
| JP | 2017-71591 A | 4/2017 |

OTHER PUBLICATIONS

International Search Report and Written Opinion from PCT/JP2018/035873 dated Dec. 18, 2018.
Zhou et al., "Organic super-electron-donors: initiators in transition metal-free haloarene-arene coupling", Chem. Sci. (2014), 5: 476-482.
Murakami et al.; "Development of new applications of SD (sodium dispersion)", Kobelco Eco-Solution Engineering Reports 14(1): Sep. 20, 2017. 26-31.
Office Action from the JPO; Japanese Patent Application No. 2019-502820 dated Mar. 5, 2019.
Extended European Search Report from EP 18862003.3 dated May 26, 2021.

* cited by examiner

*Primary Examiner* — Zinna Northington Davis
(74) *Attorney, Agent, or Firm* — Dilworth & Barrese, LLP

(57) ABSTRACT

Provided are an electron donor that is easy to handle and can be used to carry out a coupling reaction economically and efficiently through simple operations under mild conditions in a short period of time, and a method for synthesizing 4,4'-bipyridine using the electron donor. The electron donor includes a mixture of a dispersion product obtained by dispersing sodium in a dispersion solvent and 1,3-dimethyl-2-imidazolidinone, and this electron donor is used in the method for synthesizing 4,4'-bipyridine.

2 Claims, 4 Drawing Sheets

| No. | Reaction conditions | | | Analysis results | | |
|---|---|---|---|---|---|---|
| | Solvent THF:EDA | Temperature (°C) | Time (h) | Ratio (%) | | |
| | | | | Pyridine | Intermediate (M.W. 80) | 4,4'-Bipyridine |
| 1 | 1.3 : 0.7 | 50 | 3 | 73.9 | 8.1 | 17.9 |
| 2 | 1:01 | 50 | 3 | 55.3 | 12.4 | 26.3 |
| 3 | 0.7 : 1.3 | 50 | 3 | 68.9 | 4.1 | 26.9 |
| 4 | 1.3 : 0.7 | 50 | 6 | 75 | 0 | 24.9 |
| 5 | 1:01 | 50 | 6 | 76.7 | 0 | 23.3 |
| 6 | 0.7 : 1.3 | 50 | 6 | 67.3 | 0 | 32.7 |

| No. | Reaction conditions | | | Analysis results | | |
|---|---|---|---|---|---|---|
| | Solvent THF:EDA | Temperature (°C) | Time (h) | Ratio (%) | | |
| | | | | Pyridine | 2-Chloropyridine | 4,4'-Bipyridine |
| 1 | 1.3 : 0.7 | 50 | 3 | 72.2 | 0.9 | 26.8 |
| 2 | 1:01 | 50 | 3 | 55.3 | 0 | 35.9 |
| 3 | 0.7 : 1.3 | 50 | 3 | 68.9 | 0 | 36.8 |
| 4 | 1.3 : 0.7 | 50 | 6 | 69.2 | 0 | 30.7 |
| 5 | 1:01 | 50 | 6 | 63.7 | 0 | 36.2 |
| 6 | 0.7 : 1.3 | 50 | 6 | 63.4 | 0 | 36.5 |

Fig.4

| No. | Preparation conditions | | Reaction conditions | | Analysis results | | | |
|---|---|---|---|---|---|---|---|---|
| | Pyridine (mmol) | SD (mmol) | Temperature (°C) | Time (h) | Pyridine (mmol) | 4,4'-Bipyridine (mmol) | Na efficiency (%) | Pyridine balance (%) |
| 1 | 40 | 8.0 | 20 | 6 | 33 | 0.26 | 6 | 101 |
| 2 | 80 | 8.1 | 20 | 6 | 72 | 0.20 | 5 | 97 |
| 3 | 40 | 7.9 | 30 | 6 | 38 | 0.29 | 7 | 95 |
| 4 | 80 | 7.9 | 30 | 6 | 91 | 0.33 | 8 | 115 |
| 5 | 40 | 8.0 | 50 | 6 | 40 | 0.62 | 15 | 80 |
| 6 | 80 | 8.4 | 50 | 6 | 42 | 0.81 | 19 | 99 |

Fig.5

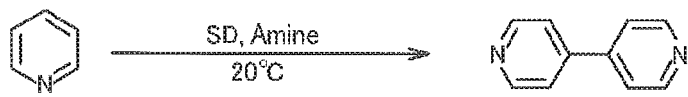

| No. | Preparation conditions | | | Reaction conditions | | Analysis results | | | |
|---|---|---|---|---|---|---|---|---|---|
| | Pyridine (mmol) | SD (mmol) | Amine (mmol) | Temperature (°C) | Time (h) | Pyridine (mmol) | 4,4'-Bipyridine (mmol) | Na efficiency (%) | Pyridine balance (%) |
| 7 | 16 | 7.8 | TMEDA 16 | 20 | 6 | 7.7 | 0.55 | 14 | 54 |
| 8 | 16 | 7.8 | TEA 16 | 20 | 6 | 12.8 | 0.20 | 5 | 82 |
| 9 | 16 | 7.8 | TMEDA 16 | 20 | 24 | 4.3 | 0.74 | 19 | 35 |
| 10 | 16 | 8 | TMEDA 8 | 20 | 24 | 10 | 0.33 | 8 | 68 |
| 11 | 40 | 2 | TMEDA 1 | 20 | 24 | 22.4 | 0.12 | 11 | 56 |
| 12 | 40 | 2 | TMEDA 2 | 20 | 24 | 18.9 | 0.06 | 6 | 48 |
| 13 | 40 | 2 | TMEDA 5 | 20 | 24 | 24.9 | 0.09 | 9 | 63 |

| No. | Preparation conditions | | Reaction conditions | | Analysis results | | | |
|---|---|---|---|---|---|---|---|---|
| | Pyridine (mmol) | SD (mmol) | Temperature (°C) | Time (h) | Pyridine (mmol) | 4,4'-Bipyridine (mmol) | Na efficiency (%) | Pyridine balance (%) |
| 1 | 40 | 8.0 | 20 | 6 | 50 | 0.45 | 11 | 127.3 |
| 2 | 40 | 8.0 | 20 | 24 | 38 | 0.51 | 13 | 97.4 |
| 3 | 40 | 4.1 | 20 | 144 | 37 | 0.39 | 19 | 95.3 |
| 4 | 80 | 4.1 | 20 | 144 | 75 | 0.84 | 41 | 95.8 |
| 5 | 120 | 4.2 | 20 | 144 | 109 | 0.32 | 15 | 91.1 |

| No. | Preparation conditions | | | | Reaction conditions | | Analysis result |
|---|---|---|---|---|---|---|---|
| | Pyridine concentration M (mol/L) | DMI (mmol) | Pyridine (mmol) | SD (mmol) | Temperature (°C) | Time (h) | Na efficiency (%) |
| 1 | 4.5 | 3.0 | 3.3 | 1 | 40 | 6 | 39 |
| 2 | 4.8 | 2.5 | 3.0 | 1 | 40 | 6 | 37 |
| 3 | 6.4 | 2.5 | 5.0 | 1 | 40 | 6 | 74 |
| 4 | 7.5 | 2.5 | 7.0 | 1 | 40 | 6 | 53 |
| 5 | 8.5 | 2.5 | 10.0 | 1 | 40 | 6 | 66 |

US 11,066,367 B2

ELECTRON DONOR, AND METHOD FOR SYNTHESIZING 4, 4'-BIPYRIDINE USING ELECTRON DONOR

TECHNICAL FIELD

The present invention relates to an electron donor, and a method for synthesizing 4,4'-bipyridine using an electron donor.

BACKGROUND ART

Coupling reactions are chemical reactions for selectively combining two molecules, particularly cyclic compounds such as aromatic compounds and aromatic heterocyclic compounds, into one molecule. For example, 4,4-bipyridine, which is one isomer of a bipyridine compound obtained by coupling pyridines to each other, can be used to synthesize a porous material through coordinated polymerization with a metal, and there are expectations regarding the application thereof to separation of $CO_2$ by absorption, and the like.

An electron donor is an example of a reagent used in a coupling reaction of aromatic compounds, aromatic heterocyclic compounds, or the like. For example, when a metal is added to a solvent such as liquid ammonia or hexamethylphosphoric triamide (which may be abbreviated as "HMPA" hereinafter), the metal dissociates into ions and electrons to produce a colored solution. It is known that, in this solution, the ion and the electron are surrounded by solvent molecules and are thus in a stable solvation state, and this solvated electron can function as a strong electron donor.

As a specific example of a coupling reaction in which a solvated electron is utilized, it is reported that 4,4'-bipyridine can be prepared through a reaction between sodium metal dissolved in HMPA, which has high electron-donating properties, and pyridine (see Patent Document 1, for example). It is also reported that a mixture of 2,2'-bipyridine, 2,4'-bipyridine, and 4,4'-bipyridine can be prepared through a reaction between sodium (having a particle diameter of 20 to 50 μm), dispersed in trimethylbenzene, and pyridine (see Patent Document 2).

Furthermore, as a technique established by the inventors of the present invention in which a coupling reaction is utilized, they report that 4,4'-di-tert-butyl-2,2'-bipyridine can be prepared through a reaction between a dispersion product obtained by dispersing sodium in a dispersion solvent and 4-tert-butylpyridine, and 4,4'-bipyridine can be prepared through a reaction between such a dispersion product and pyridine (see Patent Document 3, for example).

PRIOR ART DOCUMENTS

Patent Documents

Patent Document 1: CN 1158852 (A)
Patent Document 2: GB 957098 (A)
Patent Document 3: JP 2017-71591 A

DISCLOSURE OF THE INVENTION

Problem to be Solved by the Invention

However, ammonia, which is known as a solvent that reacts with a metal such as a sodium metal to produce a solvated electron, is difficult to handle because it has a boiling point as low as −35° C. and is a toxic reagent. In addition, HMPA disclosed in Patent Document 1 is very difficult to handle on an industrial scale because it is a carcinogenic reagent and thus jeopardizes the health of workers. Therefore, if these reagents are utilized in an industrial field, apparatuses, facilities, and the like that are suitable for handling the reagents are required, and thus problems such as an increase in cost arise. Furthermore, the reaction condition disclosed in Patent Document 1 is problematic in that the reaction time is as long as 10 hours.

Trimethylbenzene disclosed in Patent Document 2 is designated as a class 4 hazardous material under the Fire Service Act of Japan. Therefore, as is the case with ammonia and HMPA as mentioned above, if trimethylbenzene is utilized in an industrial field, apparatuses, facilities, and the like that are suitable for handling thereof are required, and thus problems such as an increase in cost arise.

With the technique disclosed in Patent Document 3 established by the inventors of the present invention, reagents that are difficult to handle are not required, and a pyridine coupling reaction can be carried out under relatively mild conditions in a short period of time. In addition, this technique is advantageous because complicated operations are not included, and the reaction is carried out through a small number of steps. However, the yield of bipyridine, which is a coupling product, is low, and there is room for further improvement in the yield.

Accordingly, it is necessary to provide an electron donor that is easy to handle and can be used to carry out an oxidation-reduction reaction such as a coupling reaction economically and efficiently through simple operations under mild conditions in a short period of time.

Means for Solving Problem

As a result of performing intensive studies to solve the foregoing problems, the inventors of the present invention found that a coupling reaction of cyclic compounds can be efficiently carried out under safe and mild conditions in a short period of time by mixing 1,3-dimethyl-2-imidazolidinone and a dispersion product obtained by dispersing sodium in a dispersion solvent, and this mixture can function as a favorable electron donor. Utilizing this makes it possible to carry out an oxidation-reduction reaction such as a coupling reaction through a small number of steps without the need for toxic or carcinogenic reagents that are difficult to handle as well as the need for complicated and expensive facilities, apparatuses, and the like. The inventors of the present invention achieved the present invention based on these findings.

That is, the present invention relates to an electron donor, and its feature is that the electron donor includes a mixture of a dispersion product obtained by dispersing sodium in a dispersion solvent, and 1,3-dimethyl-2-imidazolidinone.

With this configuration, it is possible to provide an electron donor that can be used to carry out a coupling reaction of aromatic compounds, aromatic heterocyclic compounds, or the like stably and efficiently. Furthermore, it is possible to provide an electron donor that can be utilized as a polymerization initiator. Specifically, a solvated electron is produced by adding a dispersion product obtained by dispersing sodium in a dispersion solvent to 1,3-dimethyl-2-imidazolidinone, and strong reducing power is exhibited. With this solvated electron, an oxidation-reduction reaction such as a coupling reaction can be carried out stably and efficiently, and thus a product such as a coupling product can be obtained with a high yield. With the electron donor according to this configuration, a dispersion product that is obtained by dispersing sodium in a dispersion solvent and is easy to handle is used, and therefore, an oxidation-reduction reaction such as a coupling reaction can be simply carried out through a small number of steps under mild conditions in a short period of time without the need for complicated chemical techniques. Furthermore, the electron donor does not contain toxic or carcinogenic reagents and is thus a safe electron donor, and therefore, expensive facilities, apparatuses, and the like are not needed for handling of the electron donor. Accordingly, the electron donor according to this configuration has major economical and industrial advantages. Moreover, sodium is very widely distributed throughout the earth, and therefore, this electron donor is excellent from the viewpoint of sustainability. As described above, the electron donor according to this configuration can be utilized in various technical fields such as the synthesis of functional materials (e.g., medicines, agricultural chemicals, and electronic materials).

Another feature is that, when the dispersion solvent is a nonpolar solvent that separates from the 1,3-dimethyl-2-imidazolidinone, and a specific gravity of the dispersion solvent is smaller than that of the 1,3-dimethyl-2-imidazolidinone, a lower layer of the mixture that has been divided into two layers is used as the electron donor.

With this configuration, when a nonpolar solvent that separates from 1,3-dimethyl-2-imidazolidinone so that two layers are formed and whose specific gravity is smaller than that of 1,3-dimethyl-2-imidazolidinone (specific gravity<1.05) is selected as a dispersion solvent in which sodium is dispersed to produce a dispersion product, the mixture of the dispersion product and 1,3-dimethyl-2-imidazolidinone is divided into two layers. Specifically, a layer of the dispersion solvent derived from the dispersion product is formed on a layer containing a solvated electron produced due to sodium in the dispersion product dissolving in 1,3-dimethyl-2-imidazolidinone. Accordingly, the lower layer containing the solvated electron is blocked from air, and thus the electron donor according to this configuration can be easily handled even when exposed to air. In addition, the reaction efficiency is improved. Furthermore, pouring only the lower layer portion containing the solvated electron into a reaction apparatus makes it possible to easily separate the dispersion solvent derived from the dispersion product obtained by dispersing sodium in the dispersion solvent. This makes it possible to more stably, more efficiently, and more simply carry out an oxidation-reduction reaction such as a coupling reaction, dearomatization of an aromatic ring, hydrogenation of an alkene and an alkyne, or a polymerization reaction.

Another feature is a method for synthesizing 4,4'-bipyridine in which 4,4'-bipyridine is obtained through a reaction between the electron donor according to [1] or [2] above and pyridine.

With this configuration, using the above-mentioned electron donor that can exhibit high reducing power makes it possible to efficiently and selectively synthesize 4,4'-bipyridine via a pyridine coupling reaction.

BRIEF DESCRIPTION OF THE DRAWINGS

FIG. 4 is a diagram summarizing the investigation conditions and the investigation results in Preliminary Investigation Example 3 for investigating a solvent for a coupling reaction in which pyridine was used as a substrate.

FIG. 5 is a diagram summarizing the investigation conditions and the investigation results in Preliminary Investigation Example 3 for investigating a solvent for a coupling reaction in which pyridine was used as a substrate.

BEST MODES FOR CARRYING OUT THE INVENTION

Figure 1:
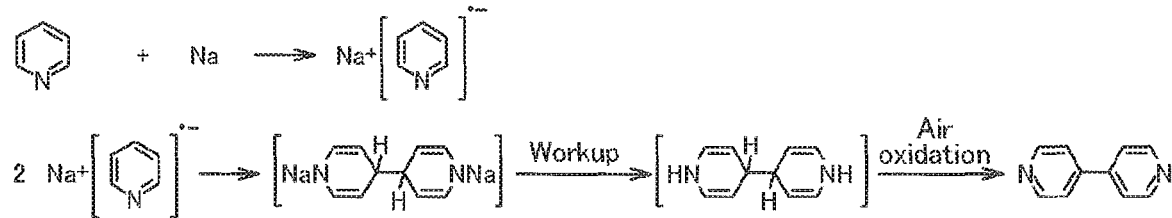
FIG. 1 is a diagram illustrating a mechanism of a reaction for synthesis of 4,4'-bipyridine through a pyridine coupling reaction, which is an example of a coupling reaction in which the electron donor according to an embodiment can be utilized.

Hereinafter, an electron donor according to an embodiment of the present invention will be described in detail. However, the present invention is not limited to the embodiment described below.

Electron Donor

An electron donor according to this embodiment includes a mixture of a dispersion product obtained by dispersing sodium in a dispersion solvent and 1,3-dimethyl-2-imidazolidinone (which may be abbreviated as "DMI" hereinafter).

The dispersion product (which may be abbreviated as "SD", an abbreviation of "Sodium Dispersion", hereinafter) obtained by dispersing sodium in a dispersion solvent is a dispersion product obtained by dispersing minute particles of sodium in an antisolvent, or a dispersion product obtained by dispersing sodium in a liquid form in an antisolvent. Sodium metal, sodium metal alloys, and the like can be used as the sodium. The average particle diameter of the minute particles is preferably less than 10 μm, and, particularly preferably, minute particles having an average particle diameter of less than 5 μm can be used. The diameter of a sphere having a projected area equal to the projected area obtained through image analyses of photomicrographs is taken as the average particle diameter.

A solvent known in the art can be used as the dispersion solvent as long as minute particles of sodium or sodium in a liquid form can be dispersed in an antisolvent, and the reaction of the coupling target compound, which is a starting compound, with the solvated electron derived from SD is not inhibited. Examples thereof include normal paraffin-based solvents such as normal decane, normal hexane, normal heptane, and normal pentane, aromatic solvents such as xylene and toluene, heterocyclic compound-based solvents such as tetrahydrothiophene, and mixed solvents thereof.

The dispersion solvent is preferably a nonpolar solvent. In this case, a mixture of the nonpolar solvent and DMI, which is a polar solvent, is divided into two layers. Furthermore, a nonpolar solvent whose specific gravity is smaller than that of DMI is preferable. In this case, a mixture of the nonpolar solvent and DMI is divided into two layers and the nonpolar solvent moves to the upper layer side. The specific gravity (20/20) of DMI is 1.0570 to 1.0590. It is preferable that the specific gravity of the dispersion solvent is smaller than that of DMI. The specific gravity of the dispersion solvent is preferably 1.05 or smaller, and more preferably 0.95 or smaller. In this case, the mixture of SD and DMI is divided into two layers, and a layer of the dispersion solvent of SD is formed on a layer containing a solvated electron produced due to sodium in SD dissolving in DMI. Accordingly, the lower layer containing the solvated electron is blocked from air, and thus the electron donor according to this embodiment can be easily handled even when exposed to air. In addition, the reaction efficiency is improved because the mixing of impurities can be suppressed. Furthermore, pouring only the lower layer containing the solvated electron into a reaction apparatus makes it possible to easily separate the dispersion solvent of SD, and thus there is no need to provide a step of separating the dispersion solvent of SD from a reaction product. This makes it possible to more stably, more efficiently, and more simply carry out an oxidation-reduction reaction such as a coupling reaction.

It is preferable to use SD having such activity that, when 2.1 molar equivalents or more of SD is reacted with chlorobenzene in a reaction solvent such as hexane, the yield of phenylsodium is 99.0% or more with respect to added chlorobenzene. Using such a highly active SD makes it possible to more efficiently carry out a coupling reaction. It is preferable to store SD in preferably a container having good gas barrier properties, such as a metal container made of stainless steel or the like or a glass vial in order to keep the activity of SD at a high level. However, a case where SD is stored in a container having poor gas barrier properties is not eliminated. In such a case, SD is used immediately (e.g., within several weeks, preferably within 3 weeks) after being manufactured.

DMI is a colorless and transparent aprotic polar solvent having a five-membered cyclic urea structure in which methyl groups are introduced to two nitrogen atoms of 2-imidazolidinone. DMI has a high flash point and is thus easy to handle. In addition, DMI has excellent solvency power, and is stable against strong acids and strong bases. Commercially available DMI or DMI manufactured using a method known in the art such as carbonylation of N,N'-dimethylethylenediamine in which N,N'-dimethylethylenediamine, obtained through a reaction between dichloroethane and methylamine, is reacted with carbon dioxide, for example, may be used.

The mixing ratio between SD and DMI in the electron donor according to this embodiment can be set as appropriate depending on the application of the electron donor and the like. DMI and SD can be mixed in such amounts that the molar ratio of DMI to SD is 1:1 to 5:1. For example, when the electron donor according to this embodiment is utilized to synthesize 4,4'-bipyridine through a pyridine coupling reaction, DMI and SD can be mixed in such amounts that the molar ratio of DMI to SD is 2:1 or more, such as 2.5:1. The substance amount of SD herein means the substance amount in terms of sodium metal contained in SD.

The electron donor according to this embodiment may be composed of a mixture of SD and DMI or various additives other than SD and DMI may be blended into the electron donor as appropriate. The additives may be used alone or in combination of two or more. There is no particular limitation on the additives as long as the function of the mixture of SD and DMI to serve as an electron donor is not impaired. Examples thereof include, but are not limited to, aromatic components, surfactants such as sorbitan trioleate, and antioxidants.

When SD and DMI are mixed, the sodium metal in sodium particles dissociates into ions and electrons, and thus the color of the solution turns bright blue. At this time, the electron is surrounded by DMI molecules and is thus brought into a stable solvation state. There is no particular limitation on the method for mixing SD and DMI as long as sodium particles contained in SD are uniformly dissolved in DMI and a stable solvated electron is produced. It is preferable that SD is added to DMI through dropping or the like, and then SD and DMI are mixed through shaking, stirring, or the like as needed. When SD and DMI are mixed, there is no particular limitation on the conditions such as the mixing time and the mixing temperature. SD and DMI can be mixed in a short period of time even at room temperature and produce a solvated electron.

On the other hand, even if a solid sodium metal is added to DMI, the sodium metal does not dissolve in DMI, and a solvated electron is not produced. Thus, the function of an electron donor is not obtained. Accordingly, the electron donor according to this embodiment can exhibit its functions only when DMI and SD are used in combination.

Utilization of Electron Donor

The electron donor according to this embodiment can be utilized for an oxidation-reduction reaction. For example, the electron donor according to this embodiment can be favorably utilized in a coupling reaction of aromatic compounds, aromatic heterocyclic compounds, or the like. It can also be favorably utilized in reduction reactions such as dearomatization of an aromatic ring and hydrogenation of an alkene and an alkyne. Furthermore, the electron donor according to this embodiment can also be favorably utilized as a polymerization initiator in a polymerization reaction.

Utilization in Coupling Reaction

There is no particular limitation on the coupling target compound, and examples thereof include aliphatic hydrocarbon compounds, alicyclic hydrocarbon compounds, alicyclic heterocyclic compounds, aromatic hydrocarbon compounds, and aromatic heterocyclic compounds, which optionally have a substituent. Aromatic compounds and aromatic heterocyclic compounds that have an aromatic ring structure are particularly preferable. Although it is preferable that a carbon-carbon bond is formed through the coupling reaction, a bond between other atoms may be formed. For example, a nitrogen-nitrogen bond may be formed. The coupling reaction may be a homo-coupling reaction or cross-coupling reaction.

The aliphatic hydrocarbon compounds may be linear or branched, and saturated or unsaturated. There is no particular limitation on the chain length. When the aliphatic hydrocarbon compounds have a substituent, there is no particular limitation on the number of substituents and the position to which a substituent is introduced. Examples of the aliphatic hydrocarbon compounds include, but are not limited to, alkanes, alkenes, and alkynes having preferably 1 to 20 carbon atoms, and more preferably 3 to 20 carbon atoms. Specific examples of the alkanes include, but are not limited to, methane, ethane, propane, n-butane, 2-methylpropane, n-pentane, 2-methylbutane, 2,2-dimethylpropane, n-hexane, 2-methylpentane, 3-methylpentane, 2,2-dimethylbutane, 2,3-dimethylbutane, n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3- trimethylbutane, n-octane, 2-methylheptane, 3-methylheptane, 4-methylheptane, 2,2-dimethylhexane, 2,3-dimethylhexane, 2,4-dimethylhexane, 2,5-dimethylhexane, 3,3-dimethylhexane, 3,4-dimethylhexane, 3-ethylhexane, 2,2,3-trimethylpentane, 2,2,4-trimethylpentane, 2,3,3-trimethylpentane, 2,3,4-trimethylpentane, 2-methyl-3-ethylpentane, 3-methyl-3-ethylpentane, 2,2,3,3-tetramethylbutane, nonane, decane, undecane, dodecane, tridecane, tetradecane, pentadecane, hexadecane, heptadecane, octadecane, nonadecane, and eicosane. Examples of the alkenes include, but are not limited to, ethylene, propylene, butene, pentene, hexene, heptene, octene, nonene, and decene. Examples of alkynes include, but are not limited to, ethyne (acetylene), propyne (methylacetylene), butyne, pentyne, hexyne, heptyne, octyne, nonyne, and decyne.

The aliphatic hydrocarbon compounds optionally have a substituent. The aliphatic hydrocarbon compounds may have one or more substituents. When the aliphatic hydrocarbon compounds have a plurality of substituents, the substituents may be the same or different. Examples of the substituents include, but are not limited to, an aliphatic hydrocarbon group, an alicyclic hydrocarbon group, a heteroalicyclic group, an aromatic hydrocarbon group, an aromatic heterocyclic group, a halogeno group, an alkoxy group, cycloalkoxy group, an aryloxy group, an aralkyloxy group, an aliphatic heterocyclicoxy group, an aromatic heterocyclicoxy group, an alkylthio group, a cycloalkylthio group, an arylthio group, an aralkylthio group, an alicyclic heterocyclothio group, an aromatic heterocyclothio group, an alkylamino group, a cycloalkylamino group, an arylamino group, an aralkylamino group, an aliphatic heterocyclicamino group, an aromatic heterocyclicamino group, an and acyl group, which optionally have a substituent.

It should be noted that examples of the aliphatic hydrocarbon groups include atomic groups obtained by removing one or more hydrogen atoms from the aliphatic hydrocarbon compounds listed above, and examples of the alicyclic hydrocarbon groups, alicyclic heterocyclic groups, aromatic hydrocarbon groups, and aromatic heterocyclic groups include atomic groups obtained by removing one or more hydrogen atoms from alicyclic hydrocarbon compounds, alicyclic heterocyclic compounds, aromatic hydrocarbon compounds, and aromatic heterocyclic compounds listed below.

Specifically, the halogeno group is a chloro group, a bromo group, a fluoro group, or an iodo group, and is preferably a chloro group.

Preferable examples of the alkoxy groups include alkoxy groups having 1 to 10 carbon atoms, and specific examples thereof include, but are not limited to, a methoxy group, an ethoxy group, a propoxy group, a butoxy group, a pentyloxy group, and a hexyloxy group. A preferable example of the cycloalkoxy groups is a cyclopropoxy group having 3 to 10 carbon atoms, and other examples thereof include a cyclobutoxy group, a cyclopentyloxy group, and a cyclohexyloxy group. Preferable examples of the aryloxy groups include aryloxy groups having 6 to 20 carbon atoms, and specific examples thereof include, but are not limited to a phenyloxy group and a naphthyloxy group. Preferable examples of the aralkyloxy groups include aralkyloxy groups having 7 to 11 carbon atoms, and specific examples thereof include a benzyloxy group and a phenethyloxy group. Examples of heterocyclic moieties of the alicyclic heterocyclic oxy groups and the aromatic heterocyclic oxy groups include alicyclic heterocyclic compounds and aromatic heterocyclic compounds listed below.

Preferable examples of the alkylthio groups include alkylthio groups having 1 to 20 carbon atoms, and examples thereof include, but are not limited to, such as a methylthio group, an ethylthio group, a propylthio group, a butylthio group, a pentylthio group, and a hexylthio group. Examples of the cycloalkylthio groups include cycloalkylthio groups having 3 to 10 carbon atoms, and specific examples thereof include, but are not limited to, such as a cyclopropylthio group, a cyclobutylthio group, a cyclopentylthio group, and a cyclohexylthio group. Preferable examples of the arylthio groups include arylthio groups having 6 to 20 carbon atoms, and specific examples thereof include, but are not limited to, a phenylthio group and a naphthylthio group. Preferable examples of the aralkylthio groups include aralkylthio groups having 7 to 11 carbon atoms, and specific examples thereof include, but are not limited to, a benzylthio group and a phenethylthio group. Examples of heterocyclic moieties of the alicyclic heterocyclic thio groups and the aromatic heterocyclic thio groups include alicyclic heterocyclic compounds and aromatic heterocyclic compounds listed below.

Regarding the alicyclic hydrocarbon compounds, the bonds between the ring forming atoms may be saturated or unsaturated, and there is no particular limitation on the number of ring members. The alicyclic hydrocarbon compounds may be monocyclic or have conjoined rings such as condensed rings and spiro rings. Examples of the alicyclic hydrocarbon compounds include, but are not limited to, cycloalkanes having preferably 3 to 10 and more preferably 3 to 7 carbon atoms, and cycloalkenyl groups having preferably 4 to 10 and more preferably 4 to 7 carbon atoms. Specific examples of the cycloalkanes include, but are not limited to, cyclopropane, cyclobutane, cyclopentane, cyclohexane, cycloheptane, and cyclooctane. Examples of the cycloalkenyl groups include, but are not limited to, a cyclopropenyl group, a cyclobutenyl group, a cyclopentenyl group, a cyclohexenyl group, a cycloheptenyl group, and a cyclooctenyl group.

The alicyclic hydrocarbon compounds optionally have a substituent. The alicyclic hydrocarbon compounds may have one or more substituents. When the alicyclic hydrocarbon compounds have a plurality of substituents, the substituents may be the same or different. There is no particular limitation on the position of a substituent. Examples of the substituents include those listed as the substituents for the aliphatic hydrocarbon compounds.

The alicyclic heterocyclic compounds are nonaromatic heterocyclic compounds that have one or more hetero atoms as ring forming atoms. The alicyclic heterocyclic compounds may be monocyclic or have conjoined rings such as condensed rings and spiro rings. The bonds between the ring forming atoms may be saturated or unsaturated, and there is no particular limitation on the number of ring members. There is no particular limitation on the hetero atoms as long as they do not react with sodium when contained as ring forming atoms. There is no particular limitation on the number and positions of the hetero atoms. Preferable examples of the hetero atoms include an oxygen atom, a nitrogen atom, and a sulfur atom. Examples of the alicyclic heterocyclic compounds include those having preferably 2 to 7 and more preferably 2 to 5 carbon atoms and preferably 1 to 5 and more preferably 1 to 3 hetero atoms. It should be noted that, when a plurality of hetero atoms is contained in an alicyclic heterocyclic compound, the hetero atoms may be the same or different. Examples of the alicyclic heterocyclic compounds include, but are not limited to, nitrogen-containing alicyclic heterocyclic compounds such as azetidine, which is a monocyclic four-membered ring compound, pyrrolidine, which is a monocyclic five-membered ring compound, and piperidine and piperazine, which are monocyclic six-membered ring compounds; oxygen-containing alicyclic heterocyclic compounds such as oxirane (oxacyclopropane), which is a monocyclic three-membered ring compound, oxetane (trimethyleneoxide), which is a monocyclic four-membered ring compound, tetrahydrofuran, which is a monocyclic five-membered ring compound, and tetrahydropyran, which is a monocyclic six-membered ring compound; sulfur-containing alicyclic heterocyclic compounds such as tetrahydrothiophene, which is a monocyclic five-membered ring compound; nitrogen-oxygen-containing alicyclic heterocyclic compounds such as morpholine, which is a monocyclic six-membered ring compound; and nitrogen-sulfur-containing alicyclic heterocyclic compounds such as thiomorpholine, which is a monocyclic six-membered ring compound.

The alicyclic heterocycles optionally have a substituent. The alicyclic heterocycles may have one or more substituents. When the alicyclic heterocycles have a plurality of substituents, the substituents may be the same or different. There is no particular limitation on the position of a substituent. Examples of the substituents include those listed as the substituents for the aliphatic hydrocarbon compounds.

There is no particular limitation on the aromatic hydrocarbon compounds as long as an aromatic ring is contained in the compound. The aromatic hydrocarbon compounds may be monocyclic or have conjoined rings such as condensed rings and spiro rings. There is no particular limitation on the number of ring members. Examples of the aromatic hydrocarbon compounds include those having preferably 6 to 22 and more preferably 6 to 14 carbon atoms. Examples of the aromatic hydrocarbon compounds include, but are not limited to, benzene which is monocyclic six-membered ring compound; naphthalene, pentalene, indene, and azulene which are bicyclic compounds; biphenylene, indacene, acenaphthylene, fluorene, phenalene, phenanthrene, and anthracene which are tricyclic compounds; fluoranthene, aceanthrylene, triphenylene, pyrene, and naphthan (tetracene) which are tetracyclic compounds; perylene and tetraphenylene which are pentacyclic compounds; pentacene which is hexacyclic compound; and rubicene, coronene, and heptacene which are heptacyclic compounds.

The aromatic hydrocarbon compounds optionally have a substituent. The aromatic hydrocarbon compounds may have one or more substituents. When the aromatic hydrocarbon compounds have a plurality of substituents, the substituents may be the same or different. There is no particular limitation on the position of a substituent. Examples of the substituents include those listed as the substituents for the aliphatic hydrocarbon compounds.

The aromatic heterocyclic compounds are aromatic heterocyclic compounds that have one or more hetero atoms as ring forming atoms. The aromatic heterocyclic compounds may be monocyclic or have conjoined rings such as condensed rings and spiro rings. There is no particular limitation on the number of ring members. There is no particular limitation on the hetero atoms as long as they do not react with sodium when contained as ring forming atoms. There is no particular limitation on the number and positions of the hetero atoms. Preferable examples of the hetero atoms include an oxygen atom, a nitrogen atom, and a sulfur atom. Examples of the aromatic heterocyclic compounds include those having preferably 1 to 5 and more preferably 3 to 5 carbon atoms and preferably 1 to 4 and more preferably 1 to 3 hetero atoms. It should be noted that, when a plurality of hetero atoms is contained in an aromatic heterocyclic compound, the hetero atoms may be the same or different.

Examples of monocyclic aromatic heterocyclic compounds include, but are not limited to, nitrogen-containing aromatic heterocyclic compounds such as pyrroline, pyrazole, pyridine, and imidazole, which are five-membered ring compounds, and pyrazine, pyrimidine, and pyridazine, which are six-membered ring compounds; oxygen-containing aromatic heterocyclic compounds such as furan, which is a five-membered ring compound; sulfur-containing aromatic heterocyclic compounds such as thiophene, which is a five-membered ring compound; nitrogen-oxygen-containing aromatic heterocyclic compounds such as oxazoline, isooxazoline, and furazan, which are five-membered ring compounds; and nitrogen-sulfur-containing aromatic heterocyclic compounds such as a thiazole group and an isothiazole group, which are five-membered ring groups. Pyridine is particularly preferable.

Examples of polycyclic aromatic heterocyclic compounds include, but are not limited to, nitrogen-containing aromatic heterocyclic compounds such as an indolizinyl group, isoindole, indole, indazole, purine, isoquinoline, quinoline, phthalazine, naphthyridine, quinoxaline, quinazoline, and cinnoline, which are bicyclic compounds; and carbazole, carboline, phenathridine, acridine, perimidine, phenanthroline, phenazine, which are tricyclic compounds; oxygen-containing aromatic heterocyclic compounds such as benzofuran, isobenzofuran, and benzopyran, which are bicyclic compounds; sulfur-containing aromatic heterocyclic compounds such as benzothiophene, which is a bicyclic compound, and thianthrene, which is a tricyclic compound; nitrogen-oxygen-containing aromatic heterocyclic compounds such as benzooxazole and benzisoxazole, which are bicyclic compounds; nitrogen-sulfur-containing aromatic heterocyclic compounds such as benzothiazole and benzoisothiazole, which are bicyclic compounds, and phenothiazine, which is a tricyclic compound; and oxygen-sulfur-containing aromatic heterocyclic compounds such as phenoxathiin, which is a tricyclic compound.

The aromatic heterocyclic compounds optionally have a substituent. The aromatic heterocyclic compounds may have one or more substituents. When the aromatic heterocyclic compounds have a plurality of substituents, the substituents may be the same or different. There is no particular limitation on the position of a substituent. Examples of the substituents include those listed as the substituents for the aliphatic hydrocarbon compounds.

The coupling reaction progresses when the coupling target compound is brought into contact with the electron donor according to this embodiment. Since the electron donor according to this embodiment contains DMI, which is an aprotic polar solvent, there is no need to further add another solvent as a reaction solvent when a coupling reaction is carried out. However, the addition of solvents known in the art such as paraffin-based solvents (e.g., normal paraffin-based solvents and cycloparaffin-based solvents), ether-based solvents, aromatic solvents, amine-based solvents, and heterocyclic compound-based solvents is not prohibited. Cyclopentyl methyl ether, 2-methyltetrahydropyrene, tetrahydrofuran, and the like can be favorably used as the ether-based solvents. Cyclohexane, normal hexane, normal decane, and the like are particularly preferable as the paraffin-based solvents. Xylene, toluene, benzene, and the like are preferable as the aromatic solvents, and halogenated aromatic solvents such as chlorobenzene and fluorobenzene can be used. Ethylenediamine and the like can be favorably used as the amine-based solvent. Tetrahydrothiophene and the like can be used as the heterocyclic compound-based solvent. These solvents may be added alone or added as a mixed solvent of two or more solvents.

The reaction temperature of the coupling reaction is not particularly limited, and can be set as appropriate depending on the types and amounts of the coupling target compound, which is a starting compound, and SD, the reaction pressure, and the like. Specifically, it is preferable that the reaction temperature is set to a temperature that is lower than the boiling points of DMI and a reaction solvent that is added as needed. Since the boiling points under increased pressure are higher than the boiling points under atmospheric pressure, the reaction temperature can be set to a higher temperature under increased pressure. The reaction can also be carried out at room temperature, and the reaction temperature is preferably 0 to 100° C., more preferably 20 to 80° C., and even more preferably room temperature to 50° C. Although there is no need to provide a special temperature controlling means for heating, cooling, and the like, a temperature controlling means may be provided as needed. The reaction may also be carried out at a low temperature, preferably about 0° C., as needed in order to suppress a side reaction and the like.

The reaction time of the coupling reaction is also not particularly limited, and it is sufficient that the reaction time is set as appropriate depending on the types and amounts of the coupling target compound, which is a starting compound, and SD, the reaction pressure, the reaction temperature, and the like. Normally, the reaction is carried out for 15 minutes to 24 hours, and preferably 20 minutes to 6 hours.

In particular, when the dispersion solvent of SD is a nonpolar solvent, the mixture of which with DMI is divided into two layers, and whose specific gravity is smaller than that of DMI, a layer of the dispersion solvent derived from SD is formed on a layer containing a solvated electron, and thus the electron donor according to this embodiment can be stably handled in the atmosphere. However, a highly active coupling intermediate and the like may be protonated due to moisture resulting from the mixing of air. Accordingly, the reaction may be carried out in an inert gas atmosphere that is filled with argon gas, nitrogen gas, or the like.

After the reaction with the electron donor according to this embodiment is complete, a target coupling product can be obtained by adding a hydrogen donor to the reaction solution to deactivate the electron donor according to this embodiment and then performing air oxidation. Materials known in the art can be used as the hydrogen donor as long as the materials provide hydrogen to a reaction product produced through the reaction with the electron donor according to this embodiment and the materials themselves are dehydrogenated. Water and alcohols can be used, for example. Preferable examples of the alcohols include lower alcohols, which have about 1 to 6 carbon atoms.

The obtained coupling product may be purified through a purification means known in the art such as column chromatography, distillation, or recrystallization. A configuration may also be employed in which the unreacted remaining coupling target compound, which is a starting compound, is collected and subjected to the coupling reaction again. This may be carried out in an inert gas atmosphere that is filled with argon gas, nitrogen gas, or the like in the same manner as in the coupling reaction.

In particular, the electron donor according to this embodiment can be preferably used in a pyridine coupling reaction. FIG. 1 is a diagram illustrating a mechanism of a reaction for synthesis of 4,4'-bipyridine through a pyridine coupling reaction. Here, an electron provided by sodium in SD is stabilized in DMI as a solvated electron. This allows the coupling reaction to progress efficiently. As described in Examples below, utilizing the electron donor according to this embodiment makes it possible to improve the yield of 4,4'-bipyridine, which is a coupling product, to 70% (as Na efficiency). Here, when the electron donor of this embodiment is reacted with pyridine, it is preferable to carry out the reaction under a condition that a ratio DMI:pyridine:SD is 1.5 to 5:3 to 7:1, particularly 2.5:5:1, for example Utilization in Reduction Reactions such as Dearomatization of Aromatic Ring and Hydrogenation of Alkene and Alkyne The electron donor according to this embodiment can be utilized in reduction reactions such as dearomatization of an aromatic ring and hydrogenation of an alkene and an alkyne. The electron donor according to this embodiment can be used instead of Birch reduction in which strong reducing power of a solvated electron produced when an alkali metal such as sodium metal is added to liquid ammonia is utilized. When the coupling target compound is brought into contact with the electron donor according to this embodiment, the reduction reaction progresses. Although there is no particular limitation on the reaction conditions of the reduction reaction such as the reaction temperature and the reaction time, the reaction conditions can be set as appropriate depending on the types and amounts of a reduction target compound, which is a starting compound, and SD, and the like, in accordance with the above-mentioned reaction conditions of the coupling reaction. It is preferable to carry out the reaction under a condition that a ratio DMI:reduction target compound:SD is 2 to 8:1:2 to 8, particularly 2 to 6:1:2 to 6, for example Utilization as Polymerization Initiator.

The electron donor according to this embodiment can be utilized as a polymerization initiator, particularly an initiator for anionic polymerization.

A compound having an electrophilic substituent can be favorably used as a polymerization target monomer. Preferable examples thereof include monomers containing an unsaturated bond in the molecule. Specific examples thereof include, but are not limited to, vinyl-based monomers such as styrene and styrene derivatives (e.g., α-methylstyrene), diene-based monomers such as butadiene, and acrylic monomers such as acrylates. The monomers may be used alone or in combination of two or more. Accordingly, the polymerization reaction may be a homopolymerization reaction or a copolymerization reaction such as a block copolymerization reaction, a random copolymerization reaction, or a graft copolymerization reaction. The electron donor according to this embodiment can be particularly preferably used as a polymerization initiator for a styrene polymerization reaction, and polystyrene can be efficiently synthesized.

The polymerization reaction progresses when the coupling target compound is brought into contact with the electron donor according to this embodiment. Although there is no particular limitation on the reaction conditions of the polymerization reaction such as the reaction temperature and the reaction time, the reaction conditions can be set as appropriate depending on the types and amounts of a monomer, which is a starting compound, and SD, and the like, in accordance with the above-mentioned reaction conditions of the coupling reaction.

A solvated electron is produced by mixing SD and DMI, and thus the electron donor according to this embodiment can exhibit strong reducing power. Accordingly, utilizing the electron donor according to this embodiment makes it possible to stably and efficiently carry out a coupling reaction of aromatic compounds, heterocyclic compounds, or the like, oxidation-reduction reactions such as dearomatization of an aromatic ring and hydrogenation of an alkene and an alkyne, and to obtain a product such as a coupling product with a high yield. Furthermore, the electron donor according to this embodiment can be used as a polymerization initiator, and thus a polymerization reaction of aromatic vinyl-based monomers such as styrene derivatives can be stably and efficiently carried out. With the electron donor according to this embodiment, SD that is easy to handle is used, and therefore, an oxidation-reduction reaction such as a coupling reaction can be simply carried out through a small number of steps under mild conditions in a short period of time without the need for complicated chemical techniques. Furthermore, the electron donor does not contain toxic or carcinogenic reagents and is thus a safe electron donor, and therefore, expensive facilities, apparatuses, and the like are not needed for handling of the electron donor. Accordingly, the electron donor according to this embodiment has major economical and industrial advantages. Moreover, sodium is very widely distributed throughout the earth, and therefore, this electron donor is excellent from the viewpoint of sustainability.

In the conventional technique, when an amine-based solvent, particularly a primary amine such as ethylenediamine or a secondary amine, is used as the solvent, SD attacks a hydrogen atom next to a nitrogen atom and thus removes a proton from the amine. As a result, a radical anion produced through the action of SD on a reaction target (substrate) returns to the original substrate. Therefore, only SD is consumed, and thus the reaction efficiency is reduced, leading to a reduction in the yield of a reaction product. On the other hand, since the electron donor of this embodiment is a mixture of DMI and SD, and DMI is a stable solvent, a problem of removal of a proton and the like, which is a problem with amine-based solvents and the like, does not arise. Thus, the electron donor of this embodiment can serve as an efficient electron donor. This makes it possible to improve the yield of a product such as a coupling product.

As described above, the electron donor according to this embodiment has strong reducing power, and can be utilized in various technical fields such as the synthesis of functional materials (e.g., medicines, agricultural chemicals, and electronic materials).

EXAMPLES

Hereinafter, the present invention will be specifically described by use of examples, but the present invention is not limited to these examples. It should be noted that, in the following examples, a dispersion product obtained by dispersing minute particles of sodium metal in normal paraffin oil was used as SD, and the substance amount of SD was a value in terms of sodium metal contained in SD.

Preliminary Investigation Example 1: Investigation of Solvent for Coupling Reaction in which Pyridine is Used as Substrate In this preliminary investigation example, the synthesis of 4,4'-bipyridine through a coupling reaction in which pyridine was used as a substrate was investigated under the investigation conditions summarized in FIG. 2. JP 2017-71591A filed by the inventors of the present invention, which is one of the prior art documents listed above, discloses that bipyridine was synthesized through a pyridine coupling reaction in which a mixed solvent of tetrahydrofuran (which may be abbreviated as "THF" hereinafter) and ethylenediamine (which may be abbreviated as "EDA" hereinafter) was used as a solvent. Therefore, in this preliminary investigation example, the synthesis of 4,4'-bipyridine through a pyridine coupling reaction was investigated by changing the ratio between THF and EDA.

Investigation Nos. 1 to 6

Pyridine (0.5 mmol) was reacted with two molar equivalents of SD. A mixed solvent of THF and EDA (THF:EDA=1.3:0.7 (Investigation Nos. 1 and 4), THF:EDA=1.0:1.0 (Investigation Nos. 2 and 5), or THF:EDA=0.7:1.3 (Investigation Nos. 3 and 6)) was used as a reaction solvent, and the reaction was carried out at 50° C. for a predetermined reaction time (3 hours (Investigation Nos. 1 to 3) or 6 hours (Investigation Nos. 4 to 6)). After the reaction was complete, the concentration of a product was measured using GC-MS, and the ratios (%) of 4,4'-bipyridine, the unreacted remaining pyridine, and an intermediate having a molecular weight of 80 (M.W.80) were calculated.

Figure 2:
FIG. 2 is a diagram summarizing the investigation conditions and the investigation results in Preliminary Investigation Example 1 for investigating a solvent for a coupling reaction in which pyridine was used as a substrate.

As a result, as shown in FIG. 2, the ratios of 4,4'-bipyridine were 17.9% (Investigation No. 1), 26.3% (Investigation No. 2), 26.9% (Investigation No. 3), 24.9% (Investigation No. 4), 23.3% (Investigation No. 5), and 2.7% (Investigation No. 6). In Investigation Nos. 1 to 6, the ratios of 4,4'-bipyridine were as low as about 20 to 30% irrespective of the investigation conditions.

Preliminary Investigation Example 2: Investigation of Solvent for Coupling Reaction in which 2-Chloropyridine is Used as Substrate Subsequently to the above-mentioned preliminary investigation example, in this preliminary investigation example, the synthesis of 4,4'-bipyridine through a coupling reaction in which 2-chloropyridine was used as a substrate was investigated under the investigation conditions summarized in FIG. 3. The synthesis of 4,4'-bipyridine through a 2-chloropyridine coupling reaction was investigated by changing the ratio between THF and EDA in a mixed solvent of THF and EDA.

Investigation Nos. 1 to 6

2-chloropyridine (0.5 mmol) was reacted with two molar equivalents of SD. A mixed solvent of THF and EDA (THF:EDA=1.3:0.7 (Investigation Nos. 1 and 4), THF:EDA=1.0:1.0 (Investigation Nos. 2 and 5), or THF:EDA=0.7:1.3 (Investigation Nos. 3 and 6)) was used as a reaction solvent, and the reaction was carried out at 50° C. for a predetermined reaction time (3 hours (Investigation Nos. 1 to 3) or 6 hours (Investigation Nos. 4 to 6)). After the reaction was complete, the concentration of a product was measured using GC-MS, and the ratios (%) of 4,4'-bipyridine, the unreacted remaining 2-chloropyridine, and pyridine were calculated.

Figure 3:
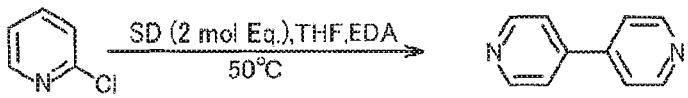
FIG. 3 is a diagram summarizing the investigation conditions and the investigation results in Preliminary Investigation Example 2 for investigating a solvent for a coupling reaction in which 2-chloropyridine was used as a substrate.

As a result, as shown in FIG. 3, the ratios of 4,4'-bipyridine were 26.8% (Investigation No. 1), 35.9% (Investigation No. 2), 36.8% (Investigation No. 3), 30.7% (Investigation No. 4), 36.2% (Investigation No. 5), 36.5% (Investigation No. 6). It can be understood that, in Investigation Nos. 1 to 6, the ratios of 4,4'-bipyridine were as low as about 30% to 40% irrespective of the investigation conditions as is the case of Preliminary Investigation Example 1.

Although not described in detail, the reaction was carried out under the conditions where the ratio between THF and EDA in the reaction solvent was set to THF:EDA=1.0:1.0 or THF:EDA=0.7:1.3 and the addition amount of SD was set to 1, 1.5, or 4 molar equivalents, and the synthesis of 4,4'- bipyridine was investigated. The ratio of 4,4'-bipyridine was about 30% to 40% irrespective of the investigation conditions, and the yield was insufficient. Moreover, when the addition amount of SD was as small as 1 molar equivalent, most (50% to 75%) of 2-chloropyridine remained unreacted.

Preliminary Investigation Example 3: Investigation of Solvent for Coupling Reaction in which Pyridine is Used as Substrate Subsequently to the above-mentioned preliminary investigation example, in this preliminary investigation example, the synthesis of 4,4'-bipyridine through a coupling reaction in which pyridine was used as a substrate was investigated under the investigation conditions summarized in FIG. 4. In this preliminary investigation example, the availability of an amine was investigated. First, the reaction was carried out by adding SD to pyridine to synthesize 4,4'-bipyridine (Investigation Nos. 1 to 6). Subsequently, the reaction was carried out in the presence of an amine-based solvent under the investigated conditions summarized in FIG. 5 to synthesize 4,4'-bipyridine (Investigation Nos. 7 to 13). Although not described in detail, it was revealed that, when a primary or secondary amine is used, SD removes a proton from the amine and a radical anion produced through the action of SD on a substrate returns to the original substrate, and therefore, only SD is consumed, leading to a reduction in Na efficiency. Accordingly, in this preliminary investigation example, a tertiary amine was used as the amine-based solvent, and the availability thereof was investigated. N,N,N',N'-tetramethylethane-1,2-diamine (which may be abbreviated as "TMEDA" hereinafter) or triethylamine (which may be abbreviated as "TEA" hereinafter) was used as the tertiary amine Investigation Nos. 1 to 6

SD (8.0 mmol (Investigation Nos. 1 and 5), 8.1 mmol (Investigation No. 2), 7.9 mmol (Investigation Nos. 3 and 4), or 8.4 mmol (Investigation No. 6)) was added to pyridine (40 mmol (Investigation Nos. 1, 3, and 5) or 80 mmol (Investigation Nos. 2, 4, and 6)) and reacted therewith at a predetermined reaction temperature (20° C. (Investigation Nos. 1 and 2), 30° C. (Investigation Nos. 3 and 4), or 50° C. (Investigation Nos. 5 and 6)) for 6 hours. After the reaction was complete, the concentrations of 4,4'-bipyridine and the unreacted remaining pyridine were measured using GC-MS, and the Na efficiency was calculated. A product was thus evaluated. Furthermore, the pyridine balance was calculated, and the evaluation was also performed from the viewpoint of a material balance.

Theoretically, 0.5 molar equivalents of bipyridine can be produced from 1 molar equivalent of SD. Accordingly, the Na efficiency can be calculated using the equation: Na efficiency (%)={2×production amount of 4,4'-bipyridine (mmol)/added SD (mmol)}×100.

The pyridine balance can be calculated using the equation: Pyridine balance (%)={(2×production amount of 4,4'-bipyridine (mmol)+collection amount of unreacted pyridine (mmol))/addition amount of pyridine (mmol)}×100

As a result, as shown in FIG. 4, the Na efficiencies were 6% (Investigation No. 1), 5% (Investigation No. 2), 7% (Investigation No. 3), 8% (Investigation No. 4), 15% (Investigation No. 5), and 19% (Investigation No. 6). In Investigation Nos. 1 to 6, the Na efficiency was about 5% to 20% irrespective of the investigation conditions. Moreover, a problem of insufficient stirring due to an increase in viscosity arose, and 2,2'-bipyridine was produced as a by-product when hexane was added to suppress the increase in viscosity.

Investigation Nos. 7 to 13

SD (7.8 mmol (Investigation Nos. 7 to 9), 8.0 mmol (Investigation No. 10), or 2.0 mmol (Investigation Nos. 11 to 13)) was added to pyridine (16 mmol (Investigation Nos. 7 to 10) or 40 mmol (Investigation Nos. 11 to 13)) in the presence of an amine (16 mmol (Investigation Nos. 7 and 9), 8 mmol (Investigation No. 10), 1 mmol (Investigation No. 11), 2 mmol (Investigation No. 12), or 5 mmol (Investigation No. 13) of TMEDA, or 16 mmol (Investigation No. 8) of TEA), and was reacted therewith at 20° C. for a predetermined reaction time (6 hours (Investigation Nos. 7 and 8) or 24 hours (Investigation Nos. 9 to 13)). After the reaction was complete, the concentrations of 4,4'-bipyridine and the unreacted remaining pyridine were measured, and the Na efficiency was calculated. A product was thus evaluated. Furthermore, the pyridine balance was calculated, and the evaluation was also performed from the viewpoint of a material balance. It should be noted that the Na efficiency and the pyridine balance were calculated as mentioned above.

As a result, as shown in FIG. 5, the Na efficiencies were 14% (Investigation No. 7), 5% (Investigation No. 8), 19% (Investigation No. 9), 8% (Investigation No. 10), 11% (Investigation No. 11), 6% (Investigation No. 12), and 9% (Investigation No. 13). The pyridine balances were 54% (Investigation No. 7), 82% (Investigation No. 8), 35% (Investigation No. 9), 68% (Investigation No. 10), 56% (Investigation No. 11), 48% (Investigation No. 12), and 63% (Investigation No. 13). It can be understood that, when a tertiary amine was added, the pyridine balance was reduced, which is not preferable from the viewpoint of the material balance, and the Na efficiency was also reduced. It is thus revealed that the addition of an amine-based solvent is not preferable.

Preliminary Investigation Example 4: Investigation of Addition Amount of SD in Coupling Reaction in which Pyridine is Used as Substrate Subsequently to the above-mentioned preliminary investigation example, in this preliminary investigation example, the synthesis of 4,4'-bipyridine through a coupling reaction in which pyridine was used as a substrate was investigated under the investigation conditions summarized in FIG. 6. 4,4'-Bipyridine was synthesized by carrying out the reaction while changing the amount of SD added to pyridine (Investigation Nos. 1 to 5).

Investigation Nos. 1 to 5

SD (8.0 mmol (Investigation Nos. 1 and 2), 4.1 mmol (Investigation Nos. 3 and 4), or 4.2 mmol (Investigation No. 5)) was added to pyridine (40 mmol (Investigation Nos. 1 to 3), 80 mmol (Investigation No. 4), or 120 mmol (Investigation No. 5)) and reacted therewith at 20° C. for a predetermined reaction time (6 hours (Investigation No. 1), 24 hours (Investigation No. 2), or 144 hours (Investigation Nos. 3 to 5)). After the reaction was complete, the concentrations of 4,4'-bipyridine and the unreacted remaining pyridine were measured, and the Na efficiency was calculated. A product was thus evaluated. Furthermore, the pyridine balance was calculated, and the evaluation was also performed from the viewpoint of a material balance. It should be noted that the Na efficiency and the pyridine balance were calculated as mentioned above.

Figure 6:
FIG. 6 is a diagram summarizing the investigation conditions and the investigation results in Preliminary Investigation Example 4 for investigating an SD addition amount for a coupling reaction in which pyridine was used as a substrate.

As a result, as shown in FIG. 6, the Na efficiencies were 11% (Investigation No. 1), 13% (Investigation No. 2), 19% (Investigation No. 3), 41% (Investigation No. 4), and 15% (Investigation No. 5). In Investigation No. 4, 0.84 mmol of 4,4'-bipyridine was synthesized from 4.1 mmol of SD, and the Na efficiency was improved to about 41%. In addition, the pyridine balance was favorable. However, a further improvement in the Na efficiency was expected.

Example 1: Coupling Reaction in which Electron Donor Containing Mixture of DMI and SD is Used and Pyridine is Used as Substrate In this example, the synthesis of 4,4'-bipyridine through a coupling reaction in which an electron donor containing a mixture of DMI and SD was used and pyridine was used as a substrate was investigated under the synthesis conditions summarized in FIG. 7.

Experiment No. 1

Figure 7:
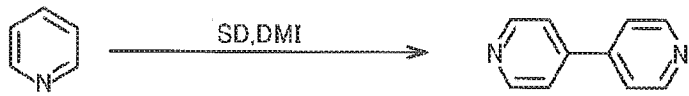
FIG. 7 is a diagram summarizing the reaction conditions and the reaction results in Example 1 in which the electron donor according to the embodiment was used to carry out a coupling reaction in which pyridine was used as a substrate.

To a flask subjected to nitrogen substitution, 3.0 mmol of DMI was added, and then 1.0 mmol of SD was dripped thereinto. When the color of the reaction solution changed from blue-green to dark green, 3.3 mmol of pyridine (4.5 M) was added thereto and the resulting solution was stirred. After the addition of pyridine, the color of the reaction solution turned reddish brown and finally turned bluish violet. When 6 hours had elapsed after the reaction at 40° C. had been started, the reaction solution was dripped into water and thus quenched. The reaction solution was allowed to stand overnight and thus subjected to air oxidation. Thereafter, solvent extraction was performed using toluene, and a product was evaluated by measuring the concentration of 4,4'-bipyridine through GC-MS and calculating the Na efficiency. It should be noted that the Na efficiency was calculated as mentioned above. As a result, as shown in FIG. 7, 4,4'-bipyridine was obtained with 39% Na efficiency.

Experiment No. 2

The reaction was carried out in the same manner as in Experiment No. 1 and the Na efficiency was calculated, except that 2.5 mmol of DMI, 1.0 mmol of SD, and 3.0 mmol (4.8 M) of pyridine were used. As a result, 4,4'-bipyridine was obtained with 37% Na efficiency.

Experiment No. 3

The reaction was carried out in the same manner as in Experiment No. 1 and the Na efficiency was calculated, except that 2.5 mmol of DMI, 1.0 mmol of SD, and 5.0 mmol (6.4 M) of pyridine were used. As a result, 4,4'-bipyridine was obtained with 74% Na efficiency.

Experiment No. 4

The reaction was carried out in the same manner as in Experiment No. 1 and the Na efficiency was calculated, except that 2.5 mmol of DMI, 1.0 mmol of SD, and 7.0 mmol (7.5 M) of pyridine were used. As a result, 4,4'-bipyridine was obtained with 53% Na efficiency.

Experiment No. 5

The reaction was carried out in the same manner as in Experiment No. 1 and the Na efficiency was calculated, except that 2.5 mmol of DMI, 1.0 mmol of SD, and 10.0 mmol (8.5 M) of pyridine were used. As a result, 4,4'-bipyridine was obtained with 66% Na efficiency.

It can be understood from the results of Experiment Nos. 1 to 5 that, when the ratio DMI:pyridine:SD was 2.5:5:1, the Na efficiency was the highest, and the coupling reaction progressed efficiently. In addition, the production of by-products such as 2,2'-bipyridine could be suppressed.

Figure 8:
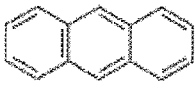
FIG. 8 is a diagram summarizing the reaction conditions and the reaction results in Example 2 in which the electron donor according to the embodiment was used to carry out a substrate reduction reaction.

Example 2: Substrate Reduction Reaction in which Electron Donor Containing Mixture of DMI and SD is Used In this example, a substrate reduction reaction in which an electron donor containing a mixture of DMI and SD was used was investigated under the synthesis conditions summarized in FIG. 8.

Experiment No. 1

To a flask subjected to nitrogen substitution, 0.5 mmol of anthracene to be used as a substrate, 3 molar equivalents of tBuOH, 6 molar equivalents of DMI, and 0.5 ml of THF were added. Then, 3 molar equivalents of SD was added to the mixture while the mixture was stirred at room temperature. Immediately after the addition of SD, the reaction solution generated heat and the color thereof turned blue, which is characteristic of SD/DMI. This color faded away in 30 seconds, and it was thus determined that the reaction was complete. After 10 minutes, methanol and water were successively added thereto to stop the reaction. The obtained product, 4a,9,9a,10-tetrahydroanthracene, was measured using $^1$H NMR, and the yield was calculated. The yield was calculated as the ratio (%) of the actually obtained product to a product that should be theoretically produced from the substrate added to the reaction system. As a result, the yield of the product was 91%.

Experiment No. 2

The reaction was carried out in the same manner as in Experiment No. 1, except that 1,2-diphenylethylene was used as a substrate. 1,2-Diphenylethane was obtained as a product, and the yield was calculated. As a result, the yield of the product 1,2-diphenylethane was 90%.

It can be understood from the results of Experiment Nos. 1 and 2 that the mixture of DMI and SD served as an electron donor, and thus the reduction reaction progressed efficiently.

INDUSTRIAL APPLICABILITY

The present invention can be favorably used in all technical fields in which an oxidation-reduction reaction using a solvated electron is utilized. The present invention can be favorably used particularly in a coupling reaction, dearomatization of an aromatic ring, hydrogenation of an alkene and an alkyne, a polymerization reaction, and the like, and is useful in fields in which functional materials such as medicines, agricultural chemicals, and electronic materials are manufactured.

The invention claimed is:

1. An electron donor comprising a mixture of a dispersion product obtained by dispersing sodium metal or sodium metal alloy in a dispersion solvent, and 1,3-dimethyl-2-imidazolidinone and wherein a lower layer of the mixture that has been divided into two layers is used as the electron donor.

2. The electron donor according to claim 1, wherein, when the dispersion solvent is a nonpolar solvent that separates from the 1,3-dimethyl-2-imidazolidinone, and a specific gravity of the dispersion solvent prior to dispersing sodium metal or sodium metal alloy therein is smaller than that of the 1,3-dimethyl-2-imidazolidinone, a lower layer of the mixture that has been divided into two layers is used as the electron donor.

* * * * *